United States Patent [19]

Dougherty et al.

[11] Patent Number: 5,468,820
[45] Date of Patent: Nov. 21, 1995

[54] REACTIVE DILUENT FOR RADIATION CURING OF FILM-FORMING POLYMERS

[75] Inventors: James A. Dougherty, Pequannock; Philip F. Wolf, Bridgewater, both of N.J.

[73] Assignee: ISP Investments Inc., Wilmington, Del.

[21] Appl. No.: 182,870

[22] Filed: Jan. 14, 1994

[51] Int. Cl.$^6$ .................. C08F 226/06; C08F 226/02; C08F 220/10

[52] U.S. Cl. .................. 526/264; 526/307.3; 526/328.5

[58] Field of Search .................. 526/264, 307.3, 526/328.5

[56] References Cited

U.S. PATENT DOCUMENTS 5,354,823  10/1994  Tseng et al. .................. 526/264

Primary Examiner—Joseph L. Schofer
Assistant Examiner—Wu C. Cheng
Attorney, Agent, or Firm—Marilyn J. Maue; Joshua J. Ward

[57] ABSTRACT

This invention relates to a reactive diluent mixture employed in a free radical polymerization of film-forming monomers which comprises between about 25 and about 90 wt. % N-vinyl lactam containing 6 to 9 carbon atoms and between about 10 and about 75 wt. % of a non-cyclic vinyl amide having from 3 to 7 carbon atoms which is employed in a concentration of between about 10 and about 50 wt. % based on total film forming monomers.

10 Claims, 2 Drawing Sheets

REACTIVE DILUENT FOR RADIATION CURING OF FILM-FORMING POLYMERS

BACKGROUND OF THE INVENTION

Various film-forming monomers are employed as coating materials and can be cured either thermally or by radiation in the presence of a free radical photoinitiator. Acrylates and methacrylates and vinyl lactams are suitable for this purpose. However, certain vinyl lactam monomers, e.g. N-vinyl caprolactams, alkyl substituted N-vinylpyrrolidones and acrylate oligomers are solids or semi-solid resins which are difficult to handle or to incorporate in reaction mixtures or to provide a uniform distribution of the monomeric or oligomeric species.

Accordingly, it is an object of this invention to provide a liquid reactive diluent for free radical induced radiation polymerizations of polymerizable monomers and oligomers.

Another object of this invention is to provide a reactive diluent which is economically and conveniently prepared from commercially available compounds.

Another object is to provide a reactive diluent capable of modifying the crosslinked density and flexibility of acrylate polymerized coatings.

Still another object is to provide a reactive diluent which is stable against discoloration and which improves adhesion to vinyl surfaces.

Yet another object is to provide a polymerizable diluent system capable of forming a terpolymeric protective coating on a substrate.

Still another object is to provide a process for coating a substrate with an improved protective coating.

These and other objects of this invention will become apparent from the following description and disclosure.

THE INVENTION

In accordance with this invention there is provided a reactive diluent mixture or blend which comprises between about 25 and about 90 wt. % of a N-vinyl lactam having from 6 to 9 carbon atoms and between about 10 and about 75 wt. % of a non-cyclic N-vinyl amide having from 3 to 7 carbon atoms. The above mixture, in the presence of a free radical and a polymerizable acrylate monomer or oligomer can be subjected to radiation curing on a substrate to provide a color stable, acid and base resistant protective coating thereon. The above blend is added and mixed with the polymerizable film-forming monomer or oligomer until a uniform mixture is obtained. The free radical polymerization of the acrylate-diluent mixture can be initiated in the presence of a photoinitiator or by electron beam where no initiator is required.

The film-forming polymerizable compounds of this invention include multifunctional acrylates and methacrylates such as urethane dimethacrylate, urethane diacrylate, di- and tri- acrylates or methacrylates of ethylene glycol, diethylene glycol di- and tri- acrylates or methacrylates and higher polyethylene glycol poly-acrylates or methacrylates, 1,3- and 1,4-dibutanediol di-acrylate or methacrylate, poly-methacrylate urethane, epoxy acrylate, polyester acrylate monomers and oligomers as well as mixtures of the above monomers and/or oligomers. In order to preserve in predominance the characteristics of the acrylate in the polymeric product, the above blend is incorporated in a concentration of between about 10 and about 40 wt. % of the total monomeric mixture; although concentrations of up to 85% are acceptable when predominance of those characteristics is unimportant.

Preferred blends of the present reactive diluent comprise between about 55 and about 85 wt. % vinyl caprolactam or vinylpyrrolidone and between about 15 to 45 wt. % N-vinyl formamide or N-vinyl-N-methylacetamide which provide liquid mixtures conveniently employed in radiation curing.

The present reactive diluent blend can be introduced into the reactor in admixture with the free radical photoinitiator, a surfactant which may be required, another non-reactive excipient or in admixture with the curable film-forming acrylate monomer or oligomer.

Curing of the present compositions can be effected in less than 1 second at or about room temperature by exposure to a source of radiation, e.g., between about 100 and about 800 millijoules/cm$^2$ of UV light, between about 0.5 and about 5 megarads of electron beam exposure or equivalent radiation exposures of gamma ray, X-ray, etc. Laser emissions can also be employed to effect curing. The above reactive diluent or compositions containing the reactive diluent are suitable for coating on a substrate such as glass, ceramic, wood, plastic, metal, vinyl, leather, paper and the like in a thickness of from about 0.1 to about 5 mils.

Suitable photoinitiators for the present invention are aromatic acyl compounds and the preferred photoinitiators are those having the formulas disclosed in Tables 1–6 of The European Coatings Journal 5/1988 on pages 350–352, i.e.

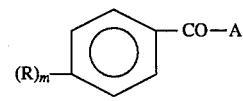

I.

where m has a value of 0 or 1; R is alkyl, $-N(CH_3)_2$, $-C_6H_5$, $-O-C_6H_5$, $-CH_2SO_3Na$ or $-CH_2N(CH_3)_3Cl$ and A is

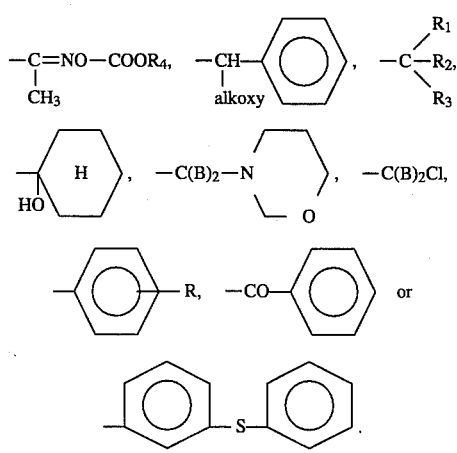

where B is hydrogen or methyl, $R_1$ and $R_3$ are independently hydrogen, $C_1$ to $C_2$ alkyl or alkoxy, $R_2$ is hydrogen, hydeoxy or phenyl and $R_4$ is $C_1$ to $C_2$ alkyl or phenyl; or

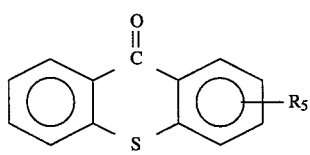

II.

where $R_5$ is chlorine or alkyl. The preferred photoinitiators of this invention are the hydroxy substituted monophenyl ketones.

The concentration of initiator in the monomeric mixture is between about 0.05 and about 5 wt. % based on total monomer.

Illustrative of a typical formulation which provides color stability, adhesion to vinyl substrates and a low freezing or solidification point includes:

1–75 wt. % of the present reactive diluent blend,
99–25 wt. % film-forming monomer and
0.5–5 wt. % free radical photoinitiator.

The film-forming compositions are easily prepared as a solution or slurry of photoinitiator, preferably in a concentration of from about 1 to about 3 wt. % and film-forming monomers followed by the addition of the present reactive diluent mixture in the desired amount with continued stirring until a clear or homogeneous solution is obtained. This procedure is normally carried out under about ambient conditions; although elevated temperatures up to about 100° C. can be employed when desired.

Optional adjuvants may be added to the composition to supply additional wetting characteristics. Suitable optional additives include wetting agents, e.g. fluorinated alkyl ester surfactants, ethoxylates of alkyl phenols, fatty alcohols, alpha-olefins, and other excipients, as desired.

The general techniques for exposing coating surfaces to radiation for curing are well known and the present compositions are cured in a conventional manner.

Having thus described the invention, reference is now had to the following Examples which illustrate specific and preferred embodiments, but which are not to be construed as limiting to the scope of the invention as more broadly described above and in the appended claims.

EXAMPLES 1–3

Comparison of Vinyl Caprolactam (VCPL), N-vinyl formamide (NVF), and a 50/50 VCPL/NVF blend as reactive diluents in the following UV curable coating formulation Components in Table I were charged into an amber bottle and mixed at room temperature until homogeneous. The formulation viscosity was measured at 25° C. Coatings were cast on the indicated substrates (1 mil coating thickness) using a #12 Mayer bar and cured by a UV exposure of 200 mJ/cm². Coating properties were determined, using standardized test methods, immediately after UV exposure. Results are summarized below:

TABLE 1

| COMPOSITION | 1 | 2 | 3 |
| --- | --- | --- | --- |
| Urethane Acrylate | 75.0 | 75.0 | 75.0 |

TABLE 1-continued

| COMPOSITION | 1 | 2 | 3 |
| --- | --- | --- | --- |
| VCPL | 25.0 | — | — |
| NVF | — | 25.0 | — |
| VCPL/NVF:50/50 | — | — | 25.0 |
| 1-hydroxycyclohexyl phenyl ketone | 3.0 | 3.0 | 3.0 |
| Viscosity (cps) | 12500 | 5200 | 6850 |
| CURED FILM PROPERTIES | | | |
| Hardness | 3H | 2H | 2H |
| % Adhesion to Polyester | 100 | 100 | 100 |
| % Adhesion to Vinyl | 100 | 0 | 25 |
| Double MEK Rubs | >100 | >100 | >100 |
| Solvent Resistance[1] | | | |
| conc. NH$_4$OH | 0 | 2 | 0 |
| 4% Acetic Acid | 0 | 0 | 0 |
| Contact Angle of Water[2] | 75.0 | 65.7 | 74.8 |

[1]ASTM D-1308, 16 hrs. at room temperature 0 = no attack, 5 = severe attack

[2]Measured by goniometer

From this example it can be seen that NVF provides the lowest viscosity to provide good leveling in the coating; however, the cured film has poor adhesion to vinyl substrates and is attacked by concentrated base. The low contact angle of water also indicates that this coating is water sensitive, i.e. it absorbs water and does not provide water fastness. Other objections to NVF are poor shelf life stability when stored under ambient conditions coupled with rapid increase of APHA color and tendency to homopolymerize during storage. VCPL, a crystalline product, is not effective at reducing viscosity of the film-forming monomer. The VCPL/NVF blend provides low viscosity, excellent resistance to water, acid and base, and shows acceptable adhesion to vinyl surfaces.

EXAMPLES 4–7

To optimize adhesion to vinyl surfaces, several VCPL/NVF ratios were evaluated in the above coating formulation. Blends containing greater than 50% VCPL show excellent adhesion.

| Example No. | VCPL/NVF ratio | % Adhesion to Vinyl |
| --- | --- | --- |
| 4 | 0/100 | 0 |
| 5 | 50/50 | 25 |
| 6 | 75/25 | 100 |
| 7 | 90/10 | 100 |

EXAMPLES 8–14

Figure 1:
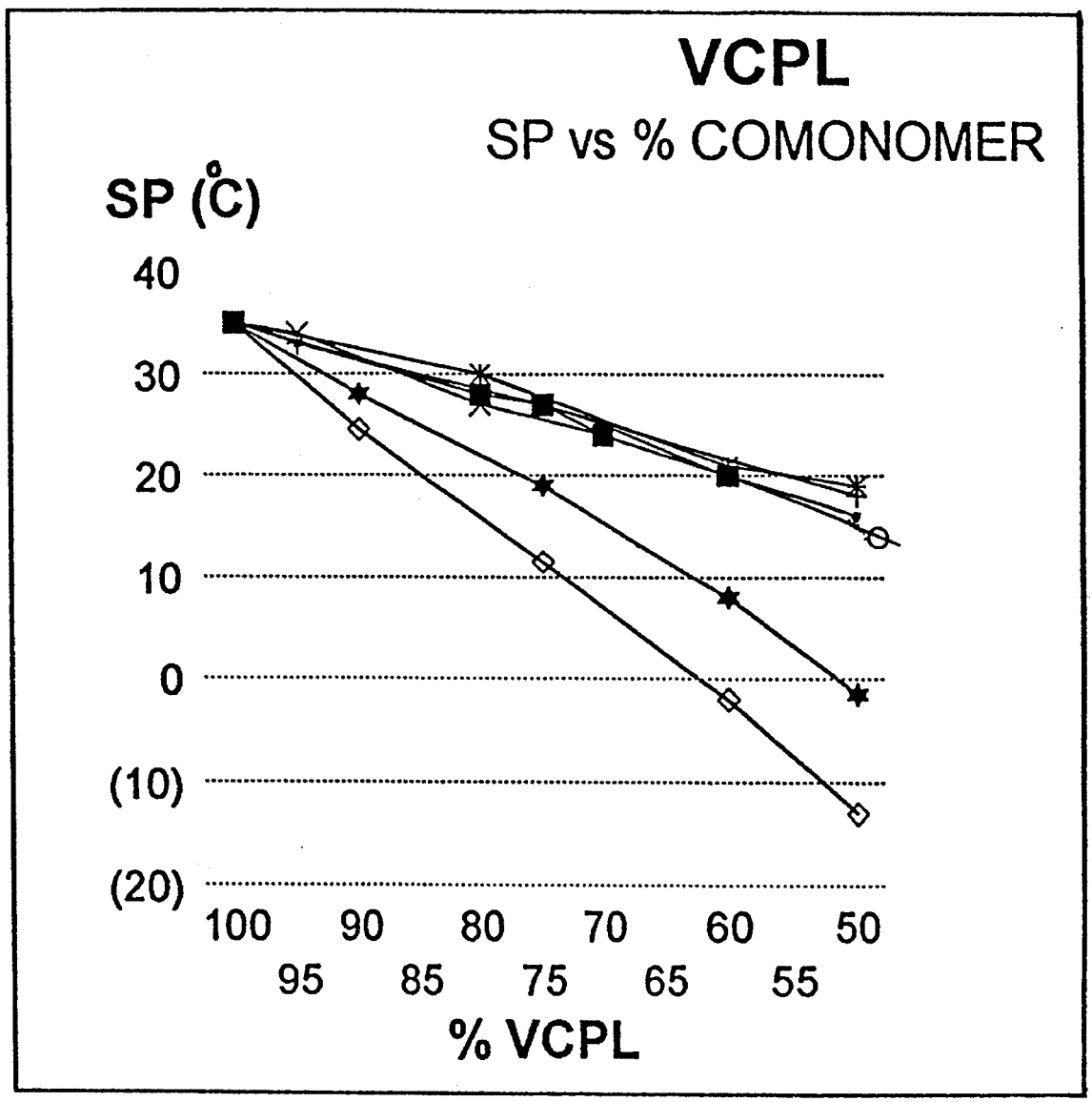
FIG. 1 compares solidification points (SP) of ethoxy-ethoxy-ethyl acrylate shown by line —●—, octadecyl acrylate by line —+—, pentaerythritol triacrylate by line —✻—, phenoxyethyl acrylate by line —■—, triethylene glycol divinyl ether by line —⊖—, N-vinyl foramide by line —⊟—, and N-vinyl-N-methyl acetamide by line —✳—.

Vinyl caprolactam (VCPL) is a crystalline solid at room temperature (freezing point=35° C.); accordingly, it must be gradually melted by warming to 50° C. so as to facilitate handling during the coating preparation. VCPL/N-vinyl amide blends remain liquid at room temperature thus providing significantly improved handling. Various amido and non-amido comonomers for VCPL were evaluated as to their ability to reduce freezing or solidification point (SP). Vinyl amides were clearly the most effective monomers evaluated since VCPL blends of these amides containing about 15% NVF or VMA (N-vinyl-N-methyl acetamide) have solidification points significantly below room temperature, FIG. 1 summarizes these findings and compares ethoxy-ethoxy-ethyl acrylate shown by line —•—; octadecyl acrylate shown by line —+—; pentaerythritol triacrylate indicated by line —✶—; phenoxyethyl acrylate indicated by line —■—; triethylene glycol divinyl ether indicated by line —⊖—; N-vinyl formamide shown by line —⊟— and N-vinyl-N-methyl acetamide shown by line —※—.

EXAMPLE 15

Figure 2:
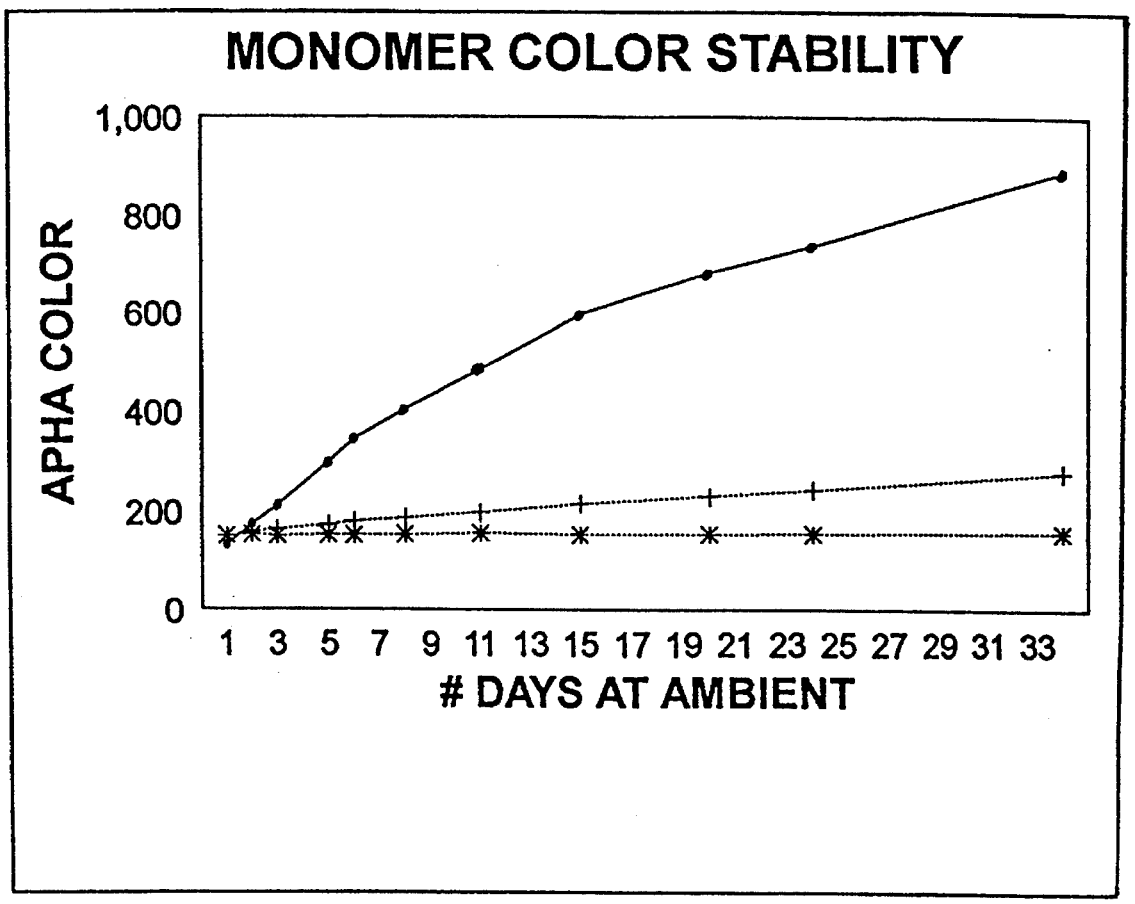
FIG. 2 shows significant improvement in color stability by blending NVF with VCPL (75/25 proportion) where NVF is indicated by line —●—, VCPL by line ✻, and the NVF/VCPL blend by line —+—.

It was found that NVF discolors quickly when stored under ambient conditions; however, blending NVF with VCPL (75/25 proportion) significantly improves color stability as shown in FIG. 2 where NVF is indicated by line —•—, VCPL by line —✶— and the NVF/VCPL blend by line —+—.

It is to be understood that other reactive diluent blends including N-vinylpyrrolidone, N-vinyl lower alkyl caprolactams and other non-cyclic N-vinyl amides within the above definitions, e.g. N-vinyl succinimide can be substituted in Example 3 to provide stable solutions suitable for radiation curing with free radical initiators.

What is claimed is:

1. A reactive diluent mixture suitable for radiation curing of an acrylate or methacrylate monomer or oligomer which comprises between about 25 and about 90 wt. % of an N-vinyl lactam containing from 6 to 9 carbon atoms and between about 10 and about 75 wt. % of a noncyclic N-vinyl amide containing from 3 to 7 carbon atoms.

2. The diluent mixture of claim 1 wherein the N-vinyl lactam is employed in a weight excess with respect to the non-cyclic N-vinyl amide.

3. The diluent mixture of claim 1 in a composition containing between about 1 and about 85 wt. % of said diluent mixture, between about 99 and about 15 wt. % of a film-forming polymerizable acrylate or methacrylate monomer or oligomer or mixture thereof and between about 0.05 and about 5 wt. % of free radical photoinitiator based on total weight monomer and/or oligomer.

4. The diluent mixture of claim 3 wherein the concentration of said acrylate or methacrylate is between about 25 and about 75 wt. % and the concentration of said free radical photoinitiator is between about 1 and about 3 wt. % of total monomer and/or total oligomer.

5. The diluent mixture of claim 1 which additionally contains a surfactant in a concentration of between about 0.05 and about 5 wt. % of said mixture.

6. The diluent mixture of claim 1 wherein said N-vinyl lactam is N-vinyl caprolactam and said N-vinyl amide is selected from the group of N-vinyl formamide and N-vinyl-N-lower alkyl acetamide.

7. The composition of claim 3 wherein said film-forming polymerizable monomer is an acrylate.

8. The composition of claim 7 wherein said acrylate is a urethanyl acrylate.

9. The composition of claim 3 wherein said diluent mixture contains an excess of said N-vinyl lactam.

10. The composition of claim 9 wherein said diluent mixture is between about 75 and about 90 wt. % N-vinyl lactam and between about 10 and about 25 wt. % non-cyclic N-vinyl amide.

* * * * *